United States Patent [19]

Bundy et al.

[11] Patent Number: 4,745,919

[45] Date of Patent: * May 24, 1988

[54] TRANSLUMINAL LYSING SYSTEM

[76] Inventors: Mark A. Bundy, 101 Pine Dr., Covington, La. 70433; Larry J. Leyser, 1611 Broadway St., New Orleans, La. 70811

[*] Notice: The portion of the term of this patent subsequent to Mar. 31, 2004 has been disclaimed.

[21] Appl. No.: 878,857

[22] Filed: Nov. 19, 1986

Related U.S. Application Data

[62] Division of Ser. No. 697,341, Feb. 1, 1985, Pat. No. 4,653,496.

[51] Int. Cl.⁴ .............................................. A61B 17/32
[52] U.S. Cl. .................................... 128/305; 128/751; 128/753; 604/22; 604/164

[58] Field of Search ............... 128/305, 751, 753, 754, 128/49-52; 604/164, 274, 264

[56] References Cited

U.S. PATENT DOCUMENTS 3,683,891 8/1972 Eskridge et al. ..................... 128/751
4,653,496 3/1987 Bundy et al. ......................... 128/305

*Primary Examiner*—Dalton L. Truluck
*Assistant Examiner*—F. Wilkens

[57] ABSTRACT

A system of surgical instruments consisting of a helically wound coil of wire having a variable axial and circumferential pitch and a concentric outer radial cutting cannula and a method for the use of the system in the removal of stenotic and occlusive lesions from the vascular lumina of living mammals.

3 Claims, 2 Drawing Sheets

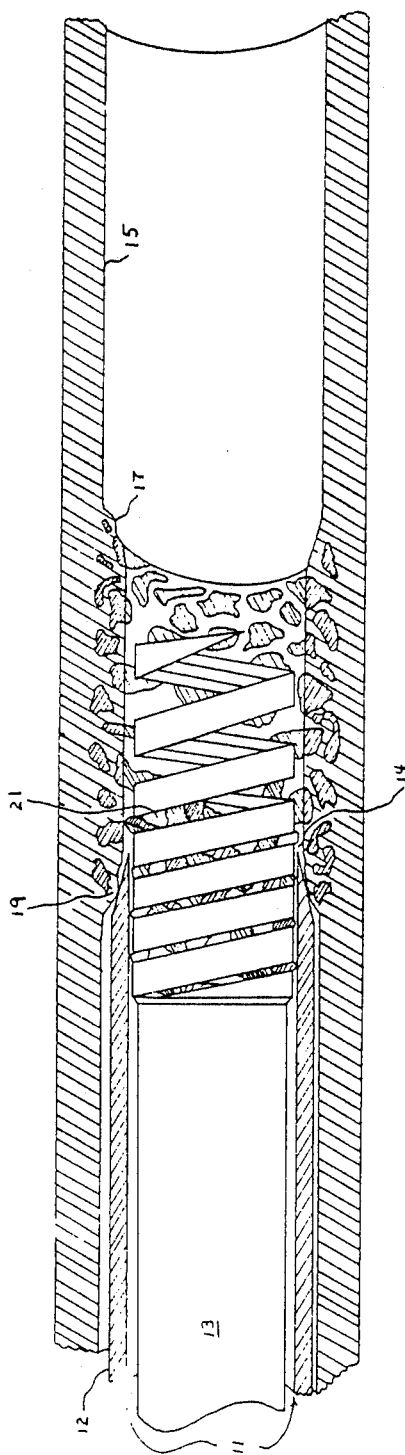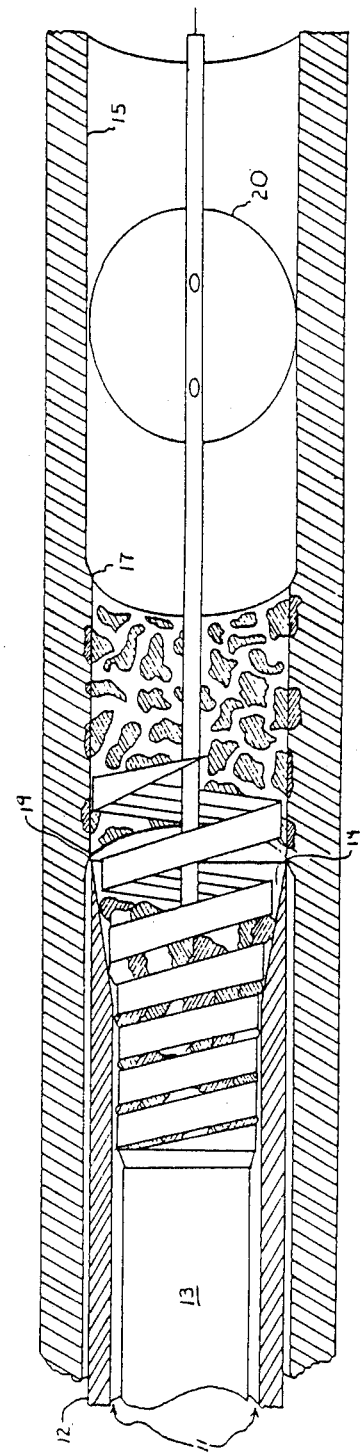

TRANSLUMINAL LYSING SYSTEM

This is a division of application Ser. No. 697,341, filed Feb. 1, 1985, now U.S. Pat. No. 4,653,496.

FIELD OF INVENTION

The transluminal lysing system relates to surgical instruments for the removal of stenotic and occlusive lesions from the vascular lumina of living mammals.

BACKGROUND

Heretofore the only commonly used methods for removing vascular occlusive lesions involved either the use of balloon catheter techniques or direct local surgical removal. Balloon catheter systems are cited in the medical literature to remove non-adhered embolic material. The limiting disadvantage of this system being the inability to remove structurally adhered material without inherent damage to the vessel wall and the distal release of fragmented lesion material causing tissue damage and loss of viability. Local surgical removal involves cutting through several layers of viable tissue or the invasion of major body cavities to reach the involved stenotic or occluded vessel. Not only does this involve the possibility of infection, pain, and loss of viable tissue, but also an increased risk of mortality. Another major disadvantage is the increased financial burden of major invasive surgery.

After a thorough search of the patent literature, several different instruments have been proposed in an unsimilar fashion to perform a similar type of function as is being set forth in this invention. It is unknown to date if any of these instruments has been reduced to common surgical practice of a clinically useful nature. Also listed in the patent literature are three inventions that have similar physical characteristics to the Transluminal Lysing System, but do not involve the same inventive concepts. The first of these is U.S. Pat. No. 2,944,552 "Surgical Instrument" issued to J. A. Cannon. This instrument is similar to the radial cutting cannula portion of the Transluminal Lysing System but has no provisions for the holding and removal of excised material. Another is U.S. Pat. No. 3,683,891 "Tissue Auger" issued to Eskridge and Wilson for the removal of core shaped biopsy samples of living tissue. The "Tissue Auger" provides no means for holding excised material under dynamic blood flow conditions. It also implies only two modes of cutting action. The Tissue Auger does not provide a smooth cutting surface and action and would therefore create torsional resistance in the excision process which is a disadvantage when working intraluminally. The Tissue Auger would not be likely to negotiate intraluminal passages without damage to the luminal walls if used in a vascular lumen. The third invention is U.S. Pat. No. 4,030,503 "Embolectomy Catheter" issued William T. Clark and is similar to the Transluminal System but provides only one cutting mode. Embolisms are usually not adhered to the lumen wall and can be removed more easily than adhered deposits. Use of an Embolectomy Catheter in an adhered deposit, as described in the above mentioned U.S. Pat. No. 4,030,503, may cause severe luminal damage or vessel rupture if the lesion is removed without complete excision prior to removal.

All three of the above mentioned instruments although similar to the Transluminal Lysing System are, to our knowledge, used under very unsimilar circumstances to remove unsimilar material from the body and as patented would not be useful in the removal of stenotic and occlusive adhered lesions of a vascular lumen.

Field of Search:
United States Classifications 128/303,303.1, 304,305.
References:

| | | |
|---|---|---|
| 812,020 | "Embalming Catheter" | Crippen |
| 843,951 | "Gape Worm Extracter" | Klock |
| 2,850,007 | "Biopsy Device" | Lingley |
| 2,994,552 | "Surgical Instrument" | Cannon |
| 3,683,891 | "Tissue Auger" | Eskridge; Wilson |
| 3,811,446 | "Erdarterectomy Apparatus" | Lerwick |
| 4,020,847 | "Rotating Cutting Catheter" | Clark |
| 4,030,503 | "Embolectomy Catheter" | Clark |
| 4,207,874 | "Laser Tunneling Device" | Choy |
| 4,290,427 | "Endarterectomy Apparatus" | Chin |
| 4,273,128 | "Coronary Cutting and Dilating Instrument" | Lary |
| 4,315,511 | "Endarterectomy Apparatus" | Chin |
| 4,445,509 | "Method and Apparatus for Removal of Enclosed Abnormal Deposits" | Auth |

OBJECTS OF THE INVENTION

The primary objective of this invention is the removal of stenotic and occlusive lesions from vascular lumina by the least invasive and least traumatic means possible. Ideally this would involve a peripheral percutaneous transluminal approach to the site of the lesion, its excision, with subsequent improvement of blood flow parameters while patient is conscious.

It is a further object of this invention of introduce multiple cutting modes for use in the removal of stenotic and occlusive lesions of varying density and material consistency.

It is a further object of this invention to remove stenotic and occlusive lesion material in as few pieces as possible to reduce the possibility of distal embolization of fragmented lesion material.

It is a further object of this invention to reduce morbidity and mortality in procedures for the removal of stenotic and occlusive lesions of the vascular system.

It is a further object of this invention to reduce the need for coronary artery bypass grafting surgery and other types of vascular bypass grafting surgery.

It is a further object of this invention to reduce the cost of treatment of vascular diseases that cause the formation of stenotic and occlusive lesions in the vascular system.

Further objects and advantages of the inventive concept described herein will be more apparent after a study of the following drawings, descriptions, and operation examples.

DETAILED DESCRIPTION OF THE DRAWINGS

FIG. 9 is an enlarged cross-section of a vascular lumen and the radial cutting cannula of FIGS. 5 and 6 to more clearly show the operation of the cutting helix of FIG. 1;

FIG. 10 is an enlarged cross-section of a vascular lumen and the radial cutting cannula of FIGS. 7 and 8 to more clearly show the operation of the spiral cutting helix of FIG. 4 along with a distally occluding balloon guiding catheter.

DETAILED PHYSICAL AND OPERATIONAL DESCRIPTION

Figure 1:
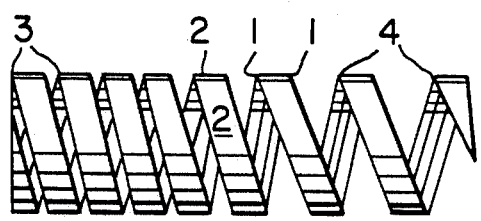
FIG. 1 is an enlarged side elevation of a cutting helix.

Referring to FIG. 1 of the drawings, the Transluminal Lysing System cutting helix is comprised of a spring wire composed of non-antigenic material whose surfaces preferrably have a low coefficient of surface roughness to reduce friction when cutting or passing through lesion material.

Figure 2:
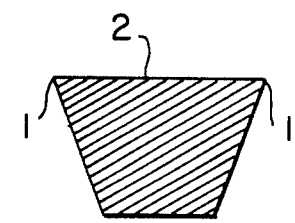
FIG. 2 is an enlarged cross-section view of the cutting helix wire of FIG. 1 at 1—1.

The spring wire from which the Transluminal Lysing System cutting helix is constructed, should have a cross-section normal to its length of a generally trapezoidal or traingular nature as shown in FIG. 2 so that when coiled to opposing obliquely sharpened corners of the wire contact or come closest to contact at the outer circumference of the helix (1) and so that the sharp edges project in the distal and proximal directions. These sharp corners forming the boundry between the inner and outer regions of the helix and functioning to separate and cut lesion material sliding between these corners.

The wire cross-section also having the property such that when coiled a helical protruding ridge is formed on the inner surface of the helix. This protruding ridge serving to impinge on lesion material entering the helix so as to enhance its retainment characteristics and also because of the ridge's helical nature it serves to propel lesion material proximally when rotated in the direction of advancing pitch. The outer surfaces of the helix (2) should appear flat and smooth so that the tool will be less likely to cause lumen wall damage when being translated to its site of operation.

Figure 3:
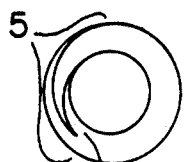
FIG. 3 is an enlarged distal end elevation of a cutting helix.

The wire is also so wrapped or coiled so that the majority of successive turns or coils of wire at the proximal end of the helix have a longitudinal or axial pitch approximately equal to the width of the wire (3) (in the distal/proximal sense of width) so as to form a closed body or bounded region, further turns or coils of wire possibly but not necessarily having a gradually increasing axial pitch toward the distal end of the helix (4). Varying the pitch of the helix serves to vary compressive cutting pressure along the length of the helix. The last turn of the wire 5 shown more fully at FIG. 3 having a sharply disposed tip and being designated as the entrance tip. In special situations (i.e. abnormal calcified lesions) a less slender and more dulled tip would be preferred to reduce the chances of the entrance tip fracturing. The entrance tip is also displaced slightly 6 in a plane almost perpendicular to the central axis of the cutting helix such that the outer circumference of the entrance tip follows the path of an imaginary involute line going toward the central axis of the cutting helix. Slight adjustments of this entrance tip displacement 6 affecting the luminal centering characteristics of the cutting helices shown in FIGS. 1 and 4. The purpose of the tip being to initially pierce the lesion material upon rotation and to then guide lesion material between the sharp cutting edges of the proximal coils.

Figure 4:
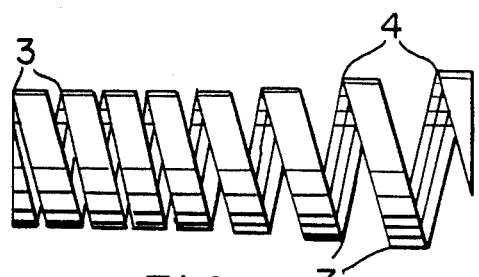
FIG. 4 is an enlarged side elevation view of a spiral cutting helix.

Another embodiment of the cutting helix which is neither a regression nor an improvement of the earlier described helix; but having distanct advantages in certain technical situations; is shown in FIG. 4. This spiral cutting helix has exactly the same structure as the earlier described cutting helix (FIG. 1), but it also comprises a spiral or circumferential pitch 7. This circumferential pitch being equal to unity for the first few proximal turns and then increasing gradually toward the distal end. This feature adds a simultaneous pulling action during excision as material is pulled away from the outer wall of the lumen toward the center of the cutting helix.

Referring to FIGS. 5–8, the Transluminal Lysing System's radial cutting cannula is a tubular body of non-antigenic material having at its distal end an outer beveled face 8 this face being so disposed so that a perpendicular surface vector extending from this face would point in the distal and radially outward directions. Another preferred embodiment of the radial cutting cannula shown clearly at FIGS. 7 and 8 has a beveled inner face 9. This face being so disposed so that a perpendicular surface vector extending from this face would point in the distal and radially inward directions. Both embodiments of the radial cutting cannula have a distally projecting radial cutting edge 10 formed on their distal ends by truncating the tip normal to the cutting cannula's central axis so as to project a circular opening. This radial cutting edge being made operational by the concentric internal relative translation and or rotation of the cutting helix and or cutting cannula. This radial cutting edge is shown in the drawings as having a sharp angular cross-section, however the inventive concepts of this invention would not be comprised of this radial cutting edge projected a small radius, squared, or other specifically advantageous edge cross-section. Edge cross-sections of a duller nature would reduce entry and translation hazards when negotiating torturous passages and turns within vessel lumens with the cutting cannula.

Figure 5:
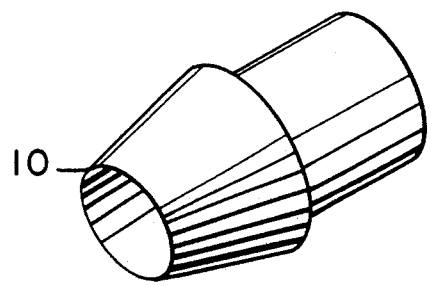
FIG. 5 is an enlarged 30 degree isometric projection of an outer beveled radial cutting cannula.
Figure 6:
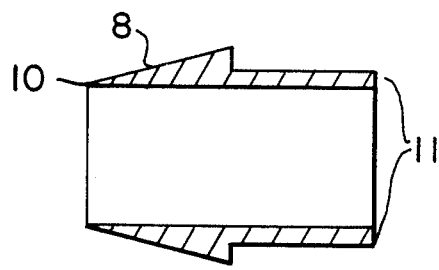
FIG. 6 is an enlarged cross-section view of an outer beveled radial cutting cannula.
Figure 7:
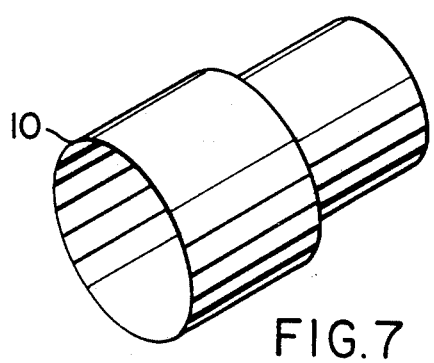
FIG. 7 is an enlarged 30 degree isometric projection of an inner beveled radial cutting cannula.
Figure 8:
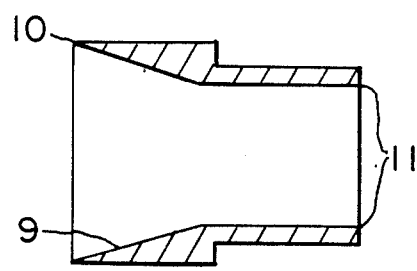
FIG. 8 is an enlarged cross-section view of an inner beveled radial cutting cannula.

Referring to FIGS. 9 and 10, both embodiments of the radial cutting cannula and cutting helices are provided with means for attachment to; or being integrally formed as part of a rigid, semi-rigid, or flexible tubing 12 13 composed of a non-antigenic material. This tubing forming a support and transport structure for the cutting helix or radial cutting cannula capable of transferring sufficient compressive, tensile, and torsional forces to produce rotational and translational motion of the cutting cannula or cutting helix. The bore of the radial cutting cannula, its support structure, attachment means is of sufficient diameter to allow the internal passage of cutting helix or spiral cutting helix 11 with varying levels of interference fit 14, this bore 11 also allowing passage of various guiding mechanisms. Depending on circumstances, a negative, zero, or positive interference fit is desirable between the outer surface of the cutting helix (FIGS. 1 and 4) and the inner surface of the cutting cannula (FIGS. 5–8). A slightly negative or non-interference (running) fit causes a cutting action similar to that of a pair of children's safety scissors which will cut stiff paper but are not likely to cut skin, this type of fit would be more useful in the removal of hard and brittle lesions. A zero or slightly positive interference fit will cause a cutting action similar to that of a pair of precision surgical scissors and will be more useful in the removal of soft pliable fatty plaques or stenosis. Higher levels of interference fit cause deformation of the cutting helix (FIGS. 1 and 4) to occur upon retraction into the cutting cannula (FIGS. 5–8) causing the cutting helix to extend and rotate in the reverse of its pitch direction. The resulting cutting action at the interface is similar to that of a sliding knife. This reverse rotation cutting action is more useful in the removal of tough stringy or fiberous material that might not be susceptible to the other cutting modes. Higher levels of interference fit also have the disadvantage of possible jamming in the outer beveled cutting cannulas (FIGS. 5 and 6).

Operational use of the Transluminal Lysing System may embody several procedural outlines depending on the specific technical situation involved. To initiate the use of this system, an entrance must be provided to gain access to the stenotic or occluded lumen 15. This can be accomplished by any of several well established techniques such as the percutaneous needle stick or direct surgical cut-down methods. Prior to the placement of any instruments, proper anticoagulation procedures will be performed. The site of the stenotic or occlusive lesion will be identified and localized using established angiographic techniques, cine angiography and fluoroscopy. In the future, other techniques that might be available for visualization and localization include direct visualization using fiber-optics or endoscopy, and indirect visualization using nuclear magnetic resonance, computed axial tomography, or digital subtraction angiography.

One of several accepted guidance techniques can then be used to advance the cutting cannula, using fluoroscopic visualization, to the site of the intraluminal lesion. These guidance techniques could include multiple intra-annular guiding wires with dull flexible tips to keep the cutting cannula centralized in the vascular lumen and to prevent vascular wall damage. Other forms of guidance could also include tubes or catheters of larger diameter than the radial cutting cannula that might be placed prior to the insertion of the radial cutting cannula. A soft plastic or rubber plug could also be inserted into the end of the radial cutting cannula to cover the cutting edge being retrievable by wire means after placement of the cutting cannula (FIGS. 5–8). A balloon catheter similar to the one shown in FIG. 10 could also be used in this manner being inflated inside the tip of the cutting cannula so that rounded surface proceeds the advancement of the cutting cannula.

After proper placement of the forward tip of the cutting cannula against one edge of the intraluminal lesion 19, the guidance systems are then removed or maintained at the operator's discretion. The use of either the cutting cannula in FIG. 5 or FIG. 7 depends on the type of intraluminal lesion and the final diameter of excision desired as compared to the actual vascular lumen diameter. The radial cutting cannula shown in FIG. 5 would be used in cases where there is a higher risk of perforation through the vessel wall such as might occur with stenotic lesions with associated ulcerative plaque but could be used in the removal of all stenosis types. The cutting cannula shown in FIG. 7 would be preferred in situations in which the stenosis is short, regular, and concentric whereby the excised portions would approximate more closely the endothelial lining of the vascular lumen as shown in FIG. 10.

The next step of the operational procedure is the addition of the cutting helix being one of two major types (FIG. 1 and FIG. 4) and several varying diameters, the choice of which depends on the type and material consistency of the particular stenotic or occlusive lesion. The outside diameter of the cutting cannula and cutting helix are chosen such that they will be slightly smaller then the diameter of the vascular lumen at the site of the stenotic or occlusive lesion. This is to prevent coring of the delicate endothelial layer of the lumen. The cutting helix is then advanced intra-annularly in the cutting cannula over the central guide wire, or balloon guidance system always using fluoroscopic visualization until the helix contacts the edge of the lesion. At this time, the cutting helix is rotated to induce advancement of the helix into the lesion material. As the helix is rotated, a spiral lysing of the lesion material is being performed by the entrance tip as it traces a helical path on the internal circumference of the stenosis. The lesion material is being simultaneously fed between the sharp edges of the trapezoidal wire extending the width of cut and further entrapping the lesion material within the continuously closing edges of the cutting helix 21. In the case of the spiral cutting helix, as material is fed between the coils as above, it is also pulled away from the lumen walls with the proximal reduction of coil diameters further enhancing later cutting action by the radial cutting cannula. This rotation is ceased upon the encountering of any increase in torsional resistance, or at which time the tip of the cutting helix has moved beyond the distal end of the lesion as verified by fluoroscopic visualization. If no increased resistance was encountered, the helix alone has completely excised the lesion core and can then be retracted through the annulus of the cutting cannula for removal from the body. If increased resistance was encountered during rotation, this indicates that total excision of the lesion has not been accomplished and lesion material is trapped between the coils of the cutting helix which may have been extended when increased resistance was encountered. Further rotation at this time could cause vessel buckling, separation of wall layers, or complete vessel failure with possibly fatal consequences.

To complete the excision process without ill-effect, the radial cutting cannula is advanced over the cutting helix using continuous or intermittent axial rotation of the cutting cannula to enhance cutting characteristics. Further enhancement of the cutting action can be obtained by slight simulataneous retraction and intermittent reverse-forward half or quarter rotations of the cutting helix. After complete separation of the core material from the remaining lesion material 17 on the vessel wall, it can then be retracted through the annulus of the radial cutting cannula with the cutting helix.

To prevent the distal flow of possible excision debris, not contained by the helix, aspiration can be maintained in process from a point outside the body on the radial cutting cannula inner lumen and/or the cutting helix inner lumen 11. The distal flow of debris can be further prevented by a number of mechanical means such as net devices, umbrella devices, or the use of balloon type catheters. Distal occlusion of the vessel lumen by use of a balloon catheter 20 or other similar device would also enhance aspiration in the lesion area by changing blood flow characteristics.

After completion of the excision process and removal of the cutting helix and lesion core, angiography is performed to determine blood flow characteristics and lumen diameter at point of lesion. The excised lesion material will also be examined and these two parameters will determine if repeat excision procedures are required; and if so what size and type of cutting helix and radial cutting cannula are needed to perform further removal.

Many of the major parameters that define the instruments actions could be monitored in process to aid in the documentation of procedure and for aiding in reproducing desired results in clinically similar circumstances. This can be effected by the addition of pressure transducing devices to the lumina of the cutting instruments or guiding catheters to measure blood pressure or translesion pressure differential. Also, strain transducers could be connected to the working support structures to monitor tensile, compressive, and torsional forces necessary to remove different types of lesion material.

When the above procedures are performed with a percutaneous peripheral entry, only local anesthetics are necessary to reduce local entry pain. Intra operative uses of this system would require higher levels of anesthesia, and the inherent higher risk factors associated with its use.

While the system just described represents a basic set of instruments and procedures for their use in the removal of stenotic and occlusive lesions from vascular lumina, it is capable of modification for nonvascular uses, all of which would embrace the inventive concepts described above. The above operative examples and preferred embodiments of the instruments should not be construed as limiting examples of this Transluminal Lysing System.

We claim:

1. A Transluminal Lysing System for the removal of stenotic and occlusive lesions from vascular lumens comprising:
    a cutting helix further comprising;
        a wire coiled helically, having a generally uniform axial pitch so as to form a tubular coil of multiple turns of wire, having a distal end and proximal end so that when the coil is engaged in lesion material rotations of the coil will induce distal longitudinal advancement of the coil,
        a means for support, translation, rotation, and communication with the coil attached to the proximal end of the coil and being of generally tubular construction of sufficient length to provide for operation of the coil from a location outside the vascular lumen,
        a sharply disposed entrance tip formed by the last distal turn of wire in the coil tip being displaced inwardly toward the central axis of the coil to provide for first cutter means as the coil is rotated into lesion material and to guide lesion material between the next proximal turn of wire as the coil is rotated,
    the wire making up the coil having;
        a cross-section normal to its length having two opposing oblique corners sharpened such that when coiled the sharpened edges project in the distal and proximal directions on each turn of the coil so as to contact or come closest to contact at the outer most circumference of the successive turns of the coil to provide for second cutting means as lesion material is passed successively from the entrance tip to the coil and between the sharpened corners, as the coil is rotated, the sharpened corners also acting as third cutting means during translation of the coil, and the wire normal cross-section also such that when coiled a continuous helical ridge or protuberance is formed on the inner surface of the coil to entrap and retain excised lesion material for removal from the vascular lumen.

2. A Transluminal Lysing System as in claim 1 further comprising:
    a radial cutting cannula comprising:
        a tubular body of solid material having a proximal and distal end,
        a bore of sufficient diameter and sufficient length to allow the internal passage of a cutting helix to and from a site of lesion from a point outside the vascular lumen,
        a distally projecting radial cutting edge attached on the distal end of the radial cutting cannula and formed by truncating the tubular body in a plane normal to its central axis so as to project a circular opening, being so beveled and sharpened so as to aid third cutter means as a cutting helix with engaged lesion material is relatively moved concentrically through the inside of the radial cutting edge during lesion removal.

3. A Transluminal Lysing System as in claim 1 or 2 further comprising:
    a cutting helix further comprising;
        a wire coiled helically and spirally to form a conical tubular coil having a distal end and proximal end, the distal end of which coil having a diameter larger than the proximal end so that when engaged in lesion material rotations will cause longitudinal advancement of the coil and will also cause material to be pulled toward the center axis of the coil along a spiral helical path.

* * * * *